US00PP20369P2

(12) United States Plant Patent
Whetman

(10) Patent No.: US PP20,369 P2
(45) Date of Patent: Sep. 29, 2009

(54) ***DIANTHUS* PLANT NAMED 'NOREEN'**

(50) Latin Name: *Dianthus×hybrida*
Varietal Denomination: NOREEN

(76) Inventor: John Whetman, Deerpark Farm, Chudleigh, Newton Abbey, Devon (GB) TQ13 0NH ( * ) Notice: Subject to any disclaimer, the term of this patent is extended or adjusted under 35 U.S.C. 154(b) by 0 days.

(21) Appl. No.: 12/220,636

(22) Filed: Jul. 24, 2008

(51) Int. Cl.
*A01H 5/00* (2006.01)

(52) U.S. Cl. ..... Plt./282

(58) Field of Classification Search ..... Plt./282
See application file for complete search history.

*Primary Examiner*—Susan B McCormick Ewoldt

(57) ABSTRACT

A new cultivar of *Dianthus* plant named 'NOREEN' that is characterized by pronounced compact habit, fine-textured grey-green foliage, and flowers that are raspberry pink with a magenta center. In combination these traits set 'NOREEN' apart from all other existing varieties of *Dianthus* known to the inventor.

2 Drawing Sheets

Genus: *Dianthus.*
Species: ×*hybrida.*
Denomination: 'NOREEN'.

BACKGROUND OF THE INVENTION

The present invention relates to a new and distinct cultivar of *Dianthus* that is grown for use as a flowering plant for pots and containers and as a hardy perennial for the garden and landscape. The new cultivar is known botanically as *Dianthus* ×*hybrida* and will be referred to hereinafter by the cultivar name 'NOREEN'.

'NOREEN' is a complex hybrid plant that is the product of a long term breeding program conducted in a greenhouse environment in Houndspool, Dawlish, Devon, United Kingdom. The primary focus of the breeding program is to produce new cultivars of *Dianthus* that exhibit unique growth habit and colors. The inventor selected 'NOREEN' in 2002 for the color combination of its flowers. 'NOREEN' exhibits a compact habit, grey-green fine foliage, and an abundance of flowers that are colored raspberry pink with a magenta center.

'NOREEN' resulted from the open pollination between *Dianthus* code name 'Whet26' as female parent, and an unknown male parent. Both parents have been raised by the inventor but have not been released or patented.

'NOREEN' is distinguishable from the female parent Whet26 as follows: whereas the female parent possesses no anthers and exhibits broad foliage, 'NOREEN' bears anthers and exhibits fine-textured foliage.

The varieties of *Dianthus* which is considered by the inventor to most closely resemble 'NOREEN' are the inventor's varieties *Dianthus* 'India Star' (unpatented) and *Dianthus* 'Alva' (co-pending application Ser. No. 12/220,635). In comparison with 'NOREEN', 'India Star' has larger flowers and a tight, compact habit. 'Alva' is approximately 20 per cent larger (height and width) than 'NOREEN', and the flowers of 'Alva' are more saturated in color.

Asexual reproduction of the new cultivar was first accomplished by the inventor in 2002 in Houndspool, Devon, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'NOREEN'. These traits in combination distinguish this cultivar from all other commercial varieties known to the inventor. 'NOREEN' has not been tested under all possible conditions and phenotypic differences may be observed with variations in environmental, climatic and cultural conditions, however, without any variance in genotype.

1. *Dianthus* 'NOREEN' exhibits a compact habit.
2. *Dianthus* 'NOREEN' blooms profusely.
3. *Dianthus* 'NOREEN' exhibits flowers that are raspberry pink with a magenta center and bloom from March through October.
4. *Dianthus* 'NOREEN' exhibits fine-textured grey-green foliage.
5. At maturity, the height of the foliage mound of *Dianthus* 'NOREEN' is 16 cm to 19 cm; the width is 13 cm to 15 cm.
6. *Dianthus* 'NOREEN' is perennial and is hardy to −15° C.
7. *Dianthus* 'NOREEN' is suitable for use as a flowering plant in pots and containers.

BRIEF DESCRIPTION OF THE DRAWINGS

The accompanying color drawings illustrate the overall appearance of the new *Dianthus* variety 'NOREEN' showing colors as true as it is reasonably possible to obtain in colored reproductions of this type. Colors in the drawings may differ from the color values cited in the detailed botanical description, which accurately describe the actual colors of the new variety 'NOREEN'.

The drawing labeled as FIG. 1 depicts an entire flowering plant.

Figure 1:
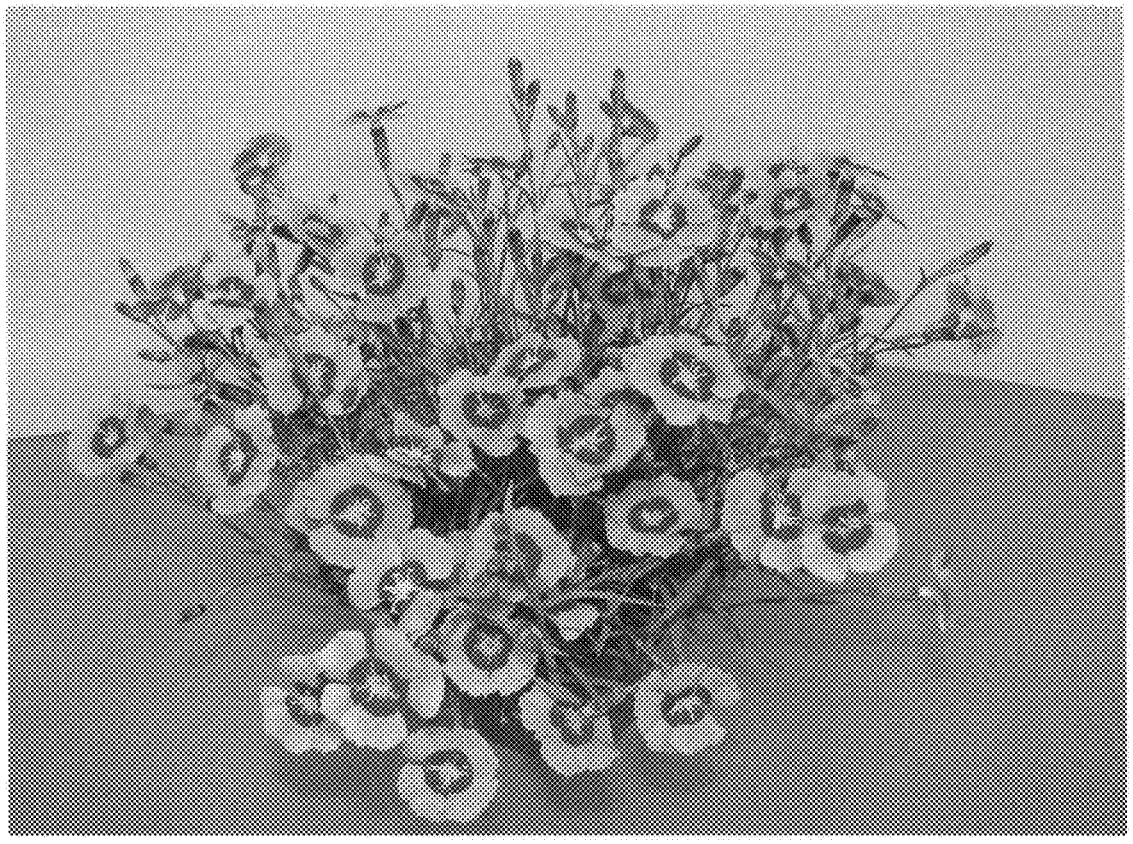
Figure 2:
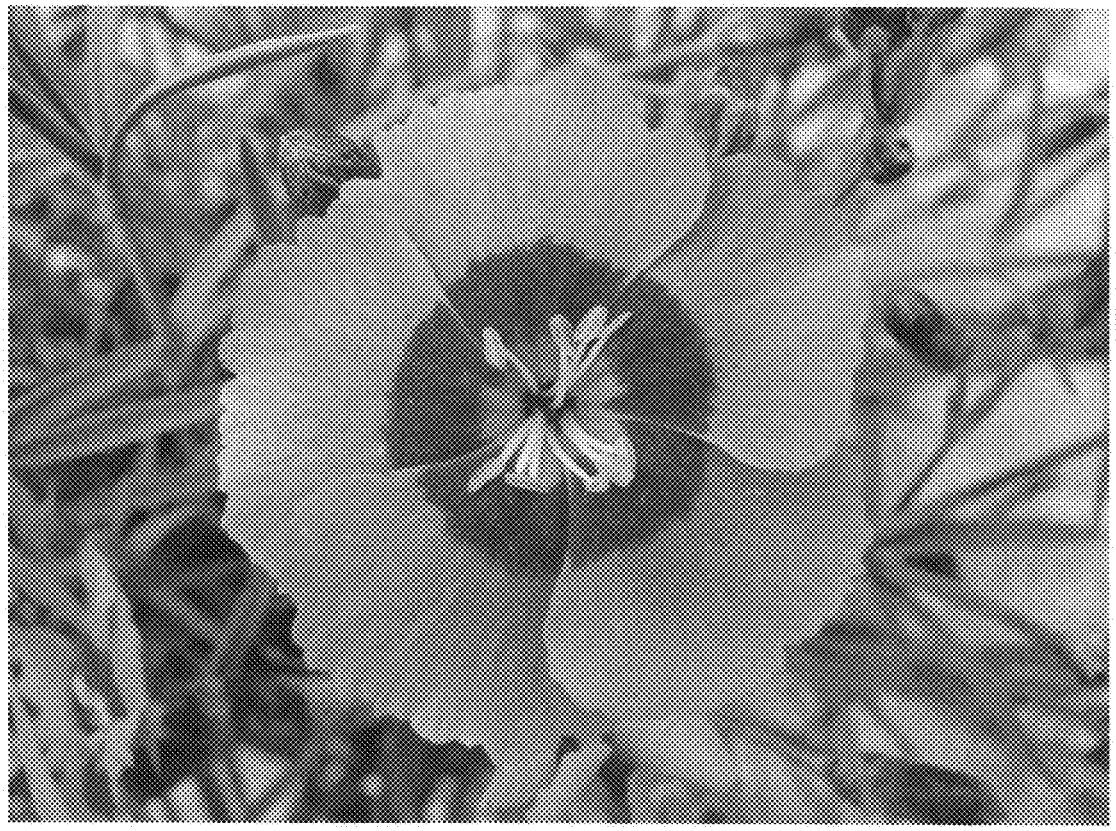

The drawing labeled as FIG. 2 depicts a close-up view of the flower.

All drawings were made of plants grown in 1.5-litre containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'NOREEN'. Data was collected in spring from 1.5-litre container plants in spring, and grown indoors in Devon, United Kingdom. The color determinations are in accordance with the 2002 edition of The Royal Horticultural Society Colour Chart, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical of other *Dianthus*.

Botanical classification: *Dianthus* 'NOREEN'.

Species: ×*hybrida*.

Common name: Dwarf *Dianthus*.

Commercial classification: *Dianthus* hybrid.

Type: Perennial.

Use: Used as a flowering plant for pots and containers and for planting in the garden or landscape.

Parentage: 'NOREEN' is a complex hybrid plant that resulted from the open pollination between the following parent plants:

*Female parent plant.*—*Dianthus* 'Whet26'.

*Male parent plant.*—Unknown.

Plant description:

*Bloom period.*—March through October.

*Plant habit.*—Compact mound with many branches and stems; upright growth.

*Plant height.*—16 cm to 19 cm after 9 months.

*Plant width.*—13 cm to 15 cm after 9 months.

*Plant hardiness.*—Hardy to minus 15° Centigrade.

*Root system.*—Fine fibrous roots.

*Propagation.*—Propagation is accomplished using vegetative cuttings.

*Cultural requirements.*—Grow in full sun, with moderate water, and well-drained moderately fertile soil. Remove dead flower heads to maintain flowering.

*Diseases and pests.*—Susceptible to known *Dianthus* pests and disease but no other susceptibilities to pests or disease are known to the inventor.

*Time and temperature needed to produce a rooted cutting.*—3 weeks are needed to produce roots on cuttings using a mist propagation unit with bottom heat of 21° Centigrade, and a minimum air temperature of 15° Centigrade.

*Crop time.*—3 months starting in the early spring through summer and 6 months starting in the fall is needed to produce a finished container size plant from a well-rooted cutting.

Stem:

*Shape.*—Cylindrical.

*Stem dimensions.*—8 cm to 12 cm in height and 2 mm to 3 mm in diameter

*Stem surface.*—Glabrous and glaucous.

*Stem color.*—145B.

*Branching.*—Numerous shoots from the axils of the lower leaves.

*Internode length.*—10 mm to 20 mm between nodes.

*Node color.*—145C.

*Node dimensions.*—3 mm in length and 4 mm in diameter.

Foliage:

*Type.*—Evergreen.

*Shape.*—Linear and straight.

*Division.*—Simple.

*Apex.*—Acute.

*Base.*—Decurrent.

*Venation.*—Not Prominent.

*Margins.*—Entire.

*Attachment.*—Sheathing.

*Arrangement.*—Opposite and spiraling.

*Surfaces* (*adaxial and abaxial*).—Glaucous.

*Leaf dimensions.*—45 mm to 55 mm in length and 3 mm to 4 mm in width.

*Leaf color* (*adaxial and abaxial surfaces*).—N189B.

*Fragrance.*—Absent.

Flowers:

*Inflorescence.*—Cymose.

*Number of flowers per stem.*—From 4 to 10.

*Peduncle dimensions.*—15 cm to 18 cm in length and 3 mm in width.

*Peduncle strength.*—Erect.

*Peduncle color.*—N189B.

*Flower development.*—In sequence from the uppermost bud.

*Flower type.*—Salviform and symmetrical.

*Flower shape.*—Circular.

*Flower profile.*—Flat.

*Flower dimensions:*(*including calyx*).—25 mm in length and 25 mm to 30 mm in width.

*Fragrance.*—Medium.

*Petals.*—Number: 5 petals. Profile: Flat. Arrangement: Persistent, single, apopetalous, overlapping. Margin: Crenate-dentate with 1 mm indentations. Texture: Soft. Shape: Obdeltoid. Surface: Slightly hairy especially in the band area. Dimensions: 35 mm in length and 20 mm in width. Color (adaxial surface): Ground color of blade: 72C. Band across blade: 61A. Middle of strap: 145C. Base of strap: 145D. Color (abaxial surface): Ground color of blade: N66D. Band across blade: No band. Middle of strap: 145C. Base of strap: 145D.

*Calyx.*—Shape: Cylindrical. Longitudinal profile: Flat. Dimensions: 15 mm to 20 mm in length and 8 mm in diameter. Sepals: Fused. Number of sepals: 5. Sepal color (both surfaces): 139C. Anthocyanin: Present. Splitting: Not observed.

*Epicalyx.*—Bracts: 1 pair of 2. Shape of outer lobe: Acuminate. Dimensions: 5 mm to 6 mm in length and 8 mm in width. Color: 136A on the tip and 143A. Anthocyanin: Present.

*Bracteoles.*—Number: 2. Dimensions: 6 mm to 8 mm in length and 8 mm in width. Color: 136A on the tip and 143A. Anthocyanin: Present.

*Lastingness of flower.*—Each individual flower lasts an average of 6 days at 20° C. on the plant.

Reproductive organs:

*Stamens*.—Number: 10. Dimensions: 10 mm–25 mm in length and 0.5 mm in diameter. Color: NN155D.

*Anthers*.—Number: 10. Dimensions: 2 mm in length and 0.5 mm in diameter. Color: 84C. Attachment: Dorsifixed.

*Pollen*.—Present. Color: 136D.

*Style*.—Number: 2. Shoulder: Absent. Color: NN155D. Dimensions: 15 mm to 20 mm in length and 0.5 mm in width.

*Stigma*.—Number: Single. Color: 70B. Dimensions: 2 mm to 3 mm above petals at maturity.

*Ovary*.—Position: Superior. Dimensions: 6 mm to 8 mm in length and 3 mm to 4 mm in diameter. Shape: Spindle. Color (adaxial): 145B. Color (abaxial): 145C.

*Seed*.—Present. Dimensions: 3 mm in length and 2 mm in diameter. Shape: Oval and flattened. Number: 1–10. Color: 202A. Surface: Crinkled.

It is claimed:

1. A new and distinct cultivar of *Dianthus* plant named 'NOREEN' as described and illustrated herein.

* * * * *